(12) United States Patent
Huh et al.

(10) Patent No.: US 10,933,252 B2
(45) Date of Patent: Mar. 2, 2021

(54) MEDICAL LIGHT DIFFUSION IMPLANT

(71) Applicants: Chang H. Huh, San Diego, CA (US); David C. Suh, Lomita, CA (US); Debbie H. Kim, La Habra Heights, CA (US); Soon H. Lee, Garden Grove, CA (US)

(72) Inventors: Chang H. Huh, San Diego, CA (US); David C. Suh, Lomita, CA (US); Debbie H. Kim, La Habra Heights, CA (US); Soon H. Lee, Garden Grove, CA (US)

( * ) Notice: Subject to any disclaimer, the term of this patent is extended or adjusted under 35 U.S.C. 154(b) by 177 days.

(21) Appl. No.: 16/026,553

(22) Filed: Jul. 3, 2018

(65) Prior Publication Data

US 2020/0009396 A1    Jan. 9, 2020

(51) Int. Cl.
*A61N 5/06* (2006.01)
*A61N 1/05* (2006.01)
(Continued)

(52) U.S. Cl.
CPC ............ *A61N 5/0601* (2013.01); *A61B 17/86* (2013.01); *A61B 18/20* (2013.01); *A61N 1/05* (2013.01);
(Continued)

(58) Field of Classification Search
CPC ...... A61N 5/06; A61N 5/0601; A61N 5/0603; A61N 5/0613; A61N 5/0622;
(Continued)

(56) References Cited

U.S. PATENT DOCUMENTS

| 2004/0121285 A1* | 6/2004 | Wu ..................... A61C 8/0069 433/173 |
| 2006/0265026 A1* | 11/2006 | Madjar ................ A61C 8/0069 607/51 |

(Continued)

FOREIGN PATENT DOCUMENTS

| JP | 2013221023 A | 10/2013 |
| KR | 1020120117769 A | 10/2012 |

(Continued)

OTHER PUBLICATIONS

Khadra M, Lyngstadaas SP, Haanaes HR, Mustafa K. Determining optimal dose of laser therapy for attachment and proliferation of human oral fibroblasts cultured on titanium implant material. J Biomed Mater Res A. 2005;73(1):55-62. doi:10.1002/jbm.a. 30270.*

(Continued)

*Primary Examiner* — Eugene T Wu
(74) *Attorney, Agent, or Firm* — Fredrikson & Byron, P.A.

(57) ABSTRACT

The present application relates to a medical light diffusion implant and, more specifically, to a functional implant to emit medical lights so as to induce rapid recovery after an implantation. According to the present invention, A medical light diffusion implant, comprising a socket including a space therein, capable of being fixed to a living body and a crown coupled with the socket so as to seal the socket, wherein the socket is transmittable by lights, and comprises a light source unit included at an inner space of the socket and the crown coupled to each other, to emit the lights.

13 Claims, 4 Drawing Sheets

(51) Int. Cl.
 *A61B 17/86* (2006.01)
 *A61B 18/20* (2006.01)
 *A61C 1/00* (2006.01)
 *A61F 2/00* (2006.01)
 *G02B 5/02* (2006.01)

(52) U.S. Cl.
 CPC ............ *A61C 1/0046* (2013.01); *A61F 2/0077* (2013.01); *A61N 2005/0659* (2013.01); *G02B 5/02* (2013.01)

(58) Field of Classification Search
 CPC .......... A61N 5/0624; A61N 2005/0602; A61N 2005/0606; A61N 2005/0612; A61N 2005/0632; A61N 2005/0635; A61N 2005/0658; A61N 2005/0659; A61N 2005/066; A61N 2005/0661; A61N 2005/0662; A61N 2005/0663
 See application file for complete search history.

(56) References Cited

U.S. PATENT DOCUMENTS

2007/0073300 A1\* 3/2007 Attawia .................. A61F 2/44
 606/328
2015/0134061 A1\* 5/2015 Friis ...................... B29C 43/003
 623/17.11

FOREIGN PATENT DOCUMENTS

KR        101734184 B1    5/2017
WO    WO-2019088939 A1 \*  5/2019

OTHER PUBLICATIONS

Muath Bani-Hani, M. Amin Karami, "Energy harvesting from mastication forces via a smart tooth," Proc. SPIE 9803, Sensors and Smart Structures Technologies for Civil, Mechanical, and Aerospace Systems 2016, 98030A (Apr. 20, 2016); https://doi.org/10.1117/12.2219390.\*

\* cited by examiner

MEDICAL LIGHT DIFFUSION IMPLANT

TECHNICAL FIELD

The present application relates to a medical light diffusion implant and, more specifically, to a functional implant to emit medical lights so as to induce rapid recovery after an implantation.

BACKGROUND ART

A medical laser radiation device can be referred by several names such as a low power laser, a cold laser, a soft laser, a photobiomodulation, a photobiostimulation, and a photostimulation device.

Laser medicine was initially identified by Endre Mester of Semmelweis University in Budapest, Hungary, who tested the effects of 694 nm low power lasers on inducing cancer in 1967, and the result of such experiment which did not induce cancer rather exhibited effects of promoting hair growth on mice, which became the first report of lasers on a biomedical stimulation. In addition, he used the laser radiation device to treat patients with non-healing skin ulcers. Since then, many researchers have suggested on a use of a variety of light sources such as lasers and LEDs (Light Emitting Diodes), and the main use of lasers was physical treatments. According to his several experiments using long pulse ruby lasers, helium neon lasers, and argon lasers, it was reported that there were effects for multiple tumor cells, hair growth, bone marrow hemoglobin synthesis, DNA/RNA synthesis of fibroblasts, wound healing and the like. In general, it was observed that a low power laser had a promotion effect whereas a high power laser had an inhibition effect, which was in line with a biphasic dose-response curve of a general medical laser radiation device.

In mid-1980s, the U.S. researchers including Abergel, Castro, etc. started the researches such as collagen generation in a fibroblast without cell damages and thermal generation using helium neon lasers, semiconductor lasers or the like. Despite of such research results reported intermittently, the research did not show significant developments throughout the U.S. and many other countries, since the equivalent effects could be achieved by various light sources other than the lasers, and furthermore the result was too varied depending on various parameters (such as wavelength, intensity, waveform, irradiation time and the like). Further, the experiments to measure objective effects were not easily achieved since spontaneous changes in tissues were not exhibited by easily measured parameters such as temperature. Therefore, its use was mainly focused on non-medical personnel rather than by medical professionals, and has been developed apart from evidence-based medicine and especially in advanced countries including the U.S. However, the main chromophores were identified recently along with theoretical developments regarding basic principles, to verify the effects and find other various indications beyond the existing pain treatment, with the effects of relatively lower power compared to laser surgical instruments to be used safely, with the expectation that its use may be increased more in the future.

Although the lasers were also started to be used for the dental treatment or medical treatment recently, the treatment cannot be performed at other times than visiting dentist or medical doctor for the treatment, and naturally the efficiency of treatment is reduced due to short period of receiving the treatment.

DISCLOSURE

Technical Problem

An object of the present invention is to provide a medical light diffusion implant capable of generating a therapeutic effect by lasers in daily life at other times than receiving a dental or medical treatment in dentistry and hospital.

Technical Solution

According to the present invention, A medical light diffusion implant, comprising a socket including a space therein, capable of being fixed to a living body and a crown coupled with the socket so as to seal the socket, wherein the socket is transmittable by lights, and comprises a light source unit included at an inner space of the socket and the crown coupled to each other, to emit the lights.

Advantageous Effect

According to the present invention, an implant may be provided to generate a therapeutic effect by medical lasers in daily life even after a dental treatment or medical treatment is completed in a dentistry or hospital.

Additionally, the present invention provides an implant capable of generating lasers continuously without a need for an additional energy supply to generate the lasers.

Additionally, the present invention may maximize the treatment time by the lasers with the improved the therapeutic effect merely by maintaining daily life, to improve user conveniences and to shorten the treatment time.

Meanwhile, the effects of the present invention are not limited to the above-mentioned effects, and may include various effects within the scope obvious to those skilled in the art based on the description set forth herein.

DESCRIPTION OF DRAWINGS

The application of the preferred embodiments of the present invention is best understood with reference to the accompanying drawings, wherein.

BEST MODE

Hereinafter, the embodiments of the present invention are illustrated in more detail with the diagrams attached herein.

The invention may be embodied in many different forms and should not be construed as being limited to the embodiments set forth herein.

It should be understood that the description hereinafter is exemplary embodiments of the present invention by way of example only, and that those skilled in the art can make various changes and modifications without departing from the scope of the present invention.

Additionally, each element may be implemented entirely in hardware or software configuration, but may also be implemented in various combinations of hardware and software performing the same function. Also, two or more elements may be implemented together by a single hardware or software.

It will be understood that the term "comprise" and variations thereof used herein are generally intended as "open" terms to be construed in an open, inclusive sense, not to exclude other additional elements.

Figure 1:
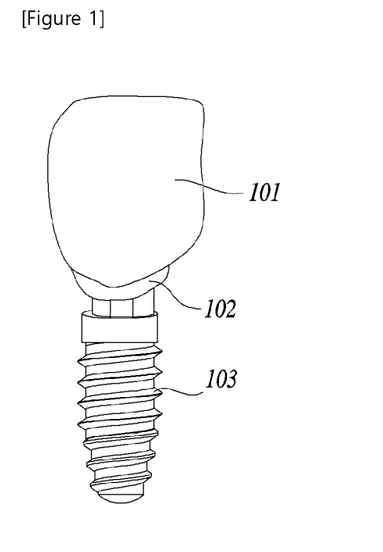
FIG. 1 shows an example of a conventional implant.

FIG. 1 shows an example of a conventional implant.

Referring to FIG. 1, the conventional implant may comprise a crown 101, an abutment 102, and a fixture 103.

The crown 101 may be fixed to a living body as being coupled with the abutment 102 or the fixture 103. The living body may include a skeleton or a bone of the living body, and may include not only the bone but also a part inside the living body. The crown 101 may cover the abutment 102 or the fixture 103 to block and seal them. An integrated body of the crown 101, the abutment 102, and the fixture 103 may function as a living body part in the living body. The living body part may include a skeleton and a bone, and the crown 101 may be bonded by an adhesive or by screw engagement with the abutment 102 or the fixture 103.

The fixture 103 may be fixed to the living body. The living body may include a skeleton or a bone of the living body, and may include not only the bone but also a part inside of the living body. The fixture 103 may be fixed to the living body by the adhesive or by screw engagement.

The abutment 102 may connect and fix the crown 101 and the fixture 103. The abutment 102 is fixedly coupled with the fixture 103 fixed to the living body and is fixedly coupled with the crown 101 to fix the implant as one body and function as a tooth.

Figure 2:
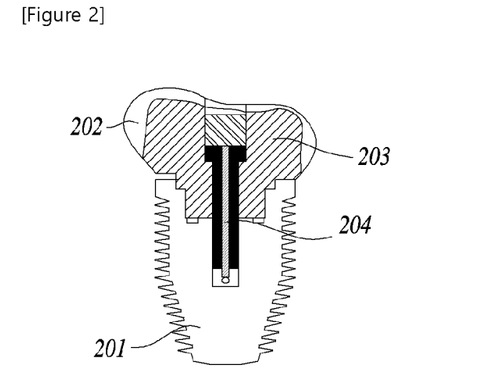
FIG. 2 shows a cross-sectional view of a medical light diffusion implant according to an embodiment of the present invention.

FIG. 2 shows a cross-sectional view of a medical light diffusion implant according to an embodiment of the present invention.

Referring to FIG. 2, the medical light diffusion implant may comprise at least one of a socket 201, a crown 202, an abutment 203, and a light source unit 204.

The socket 201 may be fixed to the living body. The living body may include a skeleton or a bone of the living body, and may include not only a bone but also a part inside the living body. The socket 201 may be fixedly coupled to the living body by the adhesive. The socket 201 may be fixedly coupled to the living body by the screw engagement. When the screw engagement is formed with helical groove on the living body such as a nut capable of engaging with a screw, the socket 201 may be rotated and inserted and coupled as the screw. The socket 201 may be more firmly coupled and fixed as the living body is recovered after being coupled with the living body. The socket 201 may pass through lights generated therein. The socket 201 may diffuse the lights generated from the inside of the socket 201 to a living tissue including skin, muscles, nerves, or bones. The socket 201 may be fixedly coupled with the crown 202, the abutment 203, and the light source unit 204.

The socket 201 may include an empty space therein. The socket 201 may include at least one of the light source unit 204 and the abutment 203. The socket 201 may include an empty space in the form of a groove in an inner part thereof.

The crown 202 may be fixedly coupled with the socket 201, the abutment 203, and the light source unit 204. The crown 202 may shield and seal the implant from the outside by coupling with the socket 201 or the abutment 203. The crown 202 may shield and seal the implant from the outside by coupling with the socket 201. The crown 202 may be formed of a metal or ceramic material. The crown 202 may be formed of gold (Au) material, but also other materials such as a material which can be used as a dental prosthesis or medical insert which would not adversely affect the living body, but not limited thereto.

The crown 202 may have a shape identical to a removed portion of the living body. The crown 202 may have a shape designed to copy a removed portion of the living body. The crown 202 may have a shape designed to copy the portion to be replaced among the living body of a user.

The crown 202 may include an empty space therein. The crown 202 may include the abutment 203 and the light source unit 204. The crown 202 may include an empty space in the form of the groove in an inner part thereof.

The abutment 203 may couple the socket 201 and the crown 202. The abutment 203 may be coupled respectively with the socket 201 and the crown 202, so as to fixedly connect them. The abutment 203 may be fixedly coupled to the socket 201 by the adhesive. The abutment 203 may be fixedly coupled to the socket 201 by the screw engagement. The abutment 203 may include an empty space therein. The abutment 203 may include a through-hole therein. The abutment 203 may include the light source unit 204 in the empty space or the through-hole.

The light source unit 204 may be included inside the implant. The light source unit 204 may be fixedly coupled with the socket 201, the crown 202, and the abutment 203. The light source unit 204 may emit lights. The lights emitted by the light source unit 204 may include a monochromatic light. The lights emitted by the light source unit 204 may include lasers. The lasers emitted by the light source unit 204 may include a light source having three properties of the lasers (i.e., monochromaticity, collimation, coherence). The light source unit 204 may emit a multi-wavelength light beam. The light source unit 204 may emit lights without damage to a tissue. The light source unit 204 may emit the low power laser without an exothermic reaction. The light source unit 204 may include the light source such as long pulse ruby lasers, helium neon lasers, argon lasers, and the like. The light source unit 204 may have effects for multiple tumor cells, hair growth, bone marrow hemoglobin synthesis, DNA/RNA synthesis of fibroblasts, wound healing and the like. The light source unit 204 may emit the low power laser. The light source unit 204 may maintain the tissue temperature at 43.5 degrees or less. The light source unit 204 may maintain the tissue temperature at 40 to 42 degrees. The light source unit 204 may maintain the tissue temperature at 39 degrees or less. The lights emitted by the light source unit 204 may include a cold laser which does not raise the temperature and a soft laser which does not cause damage to the tissue and may include the lights capable of photobiomodulation or photobiostimulation, and may include the light source which may cause a chemical change (photochemical effect) of the tissue by the lights regardless of the types of light sources such as lasers or LEDs. The light source unit 204 may be included inside of the socket 201 and the crown 202 coupled to each other, so as to perform as the abutment 203 and emit lights.

The lights generated from the light source unit 204 may cause a sequential reaction followed as chromophore after absorbing photons of the lasers so as to generate a reaction in the tissue. Cytochrome C oxidase (COX) in mitochondria may cause the reaction by absorbing the laser photons. When COX absorbs the lasers, the electron transfer is activated in a respiratory circuit as a first response, followed by increasing nitric oxide (NO) production, which will adjust the reactive oxygen species (ROS) production and transmit weak heat to the surroundings. A second response may be followed by the first response, to increase DNA/RNA synthesis, to increase adenosine triphosphate (ATP) production. Thereby, various transcription factors are induced to affect cell proliferation and migration, resulting in regulating expressions of various materials such as cytokines, growth factors and inflammatory mediators, and increased oxygen saturation of the tissue. Additionally, nitric oxide produced by the low power laser may induce vasodilation, to allow delivering via NF-kB/AP-1 route with the reactive oxygen species to induce cell proliferation and promote the generation of various growth factors.

The light source unit 204 may emit lights having a wavelength of 600 to 1200 nm in a red light region and a near infrared (NIR) region. The wavelengths below 600 nm are absorbed in hemoglobin and melanin to a large amount such that the energy is delivered to the portion other than a desired chromophore. The wavelengths of greater than 1200 nm have rapidly increased absorption as to water, which causes problem as to ensuring a sufficient depth required for the treatment. According to an embodiment, the light source unit 204 may emit the lights having the wavelength of 600 to 950 nm. According to an embodiment, the light source unit 204 may emit the lights having the wavelength of 600 to 700 nm for the tissue in a shallow depth, and lights having the wavelength of 780 to 950 nm for the tissue in a deep region. According to an embodiment, the light source unit 204 may emit the lights having four peak regions (613.5-623.5 nm, 667.5-683.7 nm, 750.7-772.3 nm, 812.5-846.0 nm).

The light source unit 204 may be included inside the socket 201, the crown 202 and the abutment 203, and may be fixed in close contact with the socket 201, the crown 202, and the abutment 203.

Figure 3:
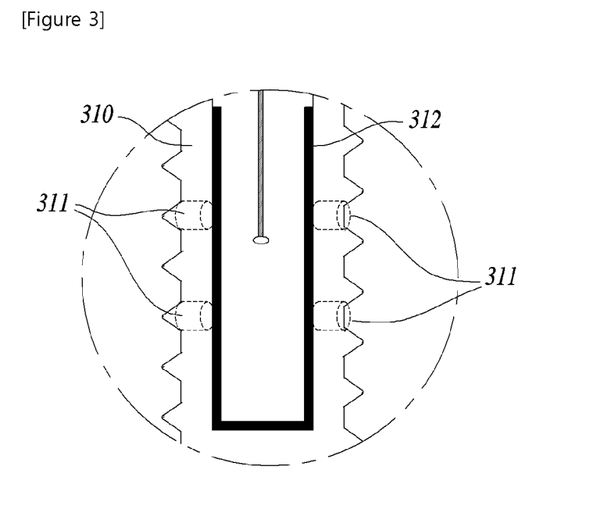
FIG. 3 shows an example of a socket included in the medical light diffusion implant according to an embodiment of the present invention.

FIG. 3 shows an example of the socket included in the medical light diffusion implant according to an embodiment of the present invention.

Referring to FIG. 3, the socket 301 of the medical light diffusion implant may comprise a through-hole 311 and a shield film 312.

The socket 301 may be fixed to the living body. The living body may include a skeleton or a bone of a living body, and may include not only a bone but also a part inside the living body. The socket 301 may be fixedly coupled to the living body by the adhesive. The socket 301 may be fixedly coupled to the living body by the screw engagement. When the screw engagement is formed with the helical groove on the living body such as a nut capable of engaging with a screw, the socket 310 may be rotated and inserted and coupled as the screw. The socket 310 may be more firmly coupled and fixed as the living body is recovered after being coupled with the living body. The socket 310 may pass through the lights generated therein. The socket 310 may diffuse the lights generated from the inside of the socket 310 to the living tissue including skin, muscles, nerves, or bones. The socket 310 may be fixedly coupled with the crown 202, the abutment 203, and the light source unit 204. The socket 301 may be formed of a metal or ceramic material. The socket 301 according to an embodiment of the present invention may be made of titanium (Ti) or titanium alloy material.

The through-hole 311 may be a through-hole connecting the inside and the outside of the socket 310. The through-hole 311 may emit the lights inside of the socket 310 to be transmitted to cells or tissues. The through-hole 311 may be included in a single number. According to an embodiment of the present invention, the through-hole 311 may be formed in a shape in which a lower hemisphere of the socket 310 is removed. That is, the inner space of the socket 310 may be formed as the through-hole. According to an embodiment of the present invention, a plurality of through-holes 311 may be included. The through-holes 311 may be formed and included on a side surface of the socket 310, as a single or a plurality of through-holes 311. The through-holes 311 are included as a plurality of holes on the side surface of the socket 310 so that the lights generated in the socket 310 may pass through the socket 310 to reach the cells or the tissues.

The shield film 312 may prevent foreign substances from entering into the socket 310. The shield film 312 may be included in the socket 310. The shield film 312 may be engaged with and fixed to the inner surface of the socket 310. The shield film 312 may allow the lights generated in the socket 310 to pass through so as to be radiated to the outside, and to prevent the foreign substances from flowing into the socket 310. The shield film 312 may be formed of a transparent light-transmitting material. The shield film 312 may be made of glass, ceramics or plastic.

Figure 4:
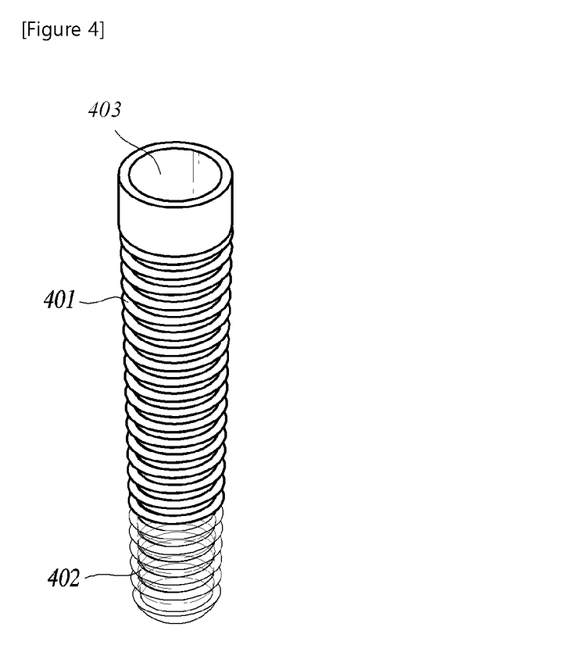
FIG. 4 shows an example of a socket included in the medical light diffusion implant according to an embodiment of the present invention.

FIG. 4 shows an example of the socket included in the medical light diffusion implant according to an embodiment of the present invention.

Referring to FIG. 4, the socket 401 of the medical light diffusion implant may comprise a light transmitting part 402 and an inner space 403.

The light transmitting part 402 may transmit the lights generated in the inner space 403 of the socket 401 to the outside of the socket 401. The light transmitting part 402 may be coupled and fixed to a portion of the socket 401. The light transmitting part 402 may be coupled and fixed to a lower portion of the socket 401. The light transmitting part 402 allows the lights generated in the socket 401 to pass through so as to be radiated to the outside of the socket 401, and to prevent the foreign substances from flowing into the socket 401. The light transmitting part 402 may be formed of the transparent or light-transmitting material. The light transmitting part 402 may be made of glass, ceramics or plastic.

The inner space 403 may comprise the light source unit 204. The light source unit may be fixedly attached or coupled to the inner space 403.

Figure 5:
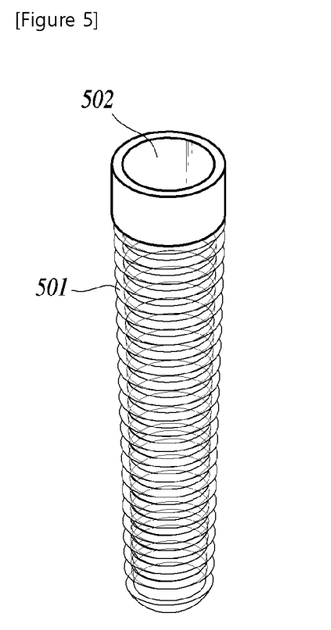
FIG. 5 shows an example of a socket included in the medical light diffusion implant according to an embodiment of the present invention.

FIG. 5 shows an example of the socket included in the medical light diffusion implant according to an embodiment of the present invention.

Referring to FIG. 5, the socket 501 of the medical light diffusion implant may comprise the inner space 502.

The socket 501 may transmit the lights generated in the inner space 403 of the socket 501 to be transmitted to the outside of the socket 501. The socket 501 allows the lights generated inside to pass through so as to be radiated to the outside of the socket 501, and to prevent the foreign substances from flowing into the socket 501. The socket 501 may be entirely formed of a transparent or light-transmitting material. The socket 501 may be made of glass, ceramics or plastic.

The inner space 502 may comprise the light source unit 204. The light source unit may be fixedly attached or coupled to the inner space 502.

Figure 6:
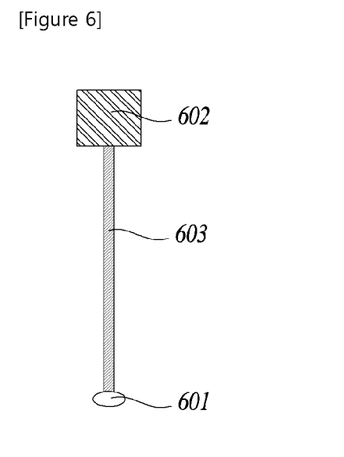
FIG. 6 shows an example of a light source unit included in the medical light diffusion implant according to an embodiment of the present invention.

FIG. 6 shows an example of the light source unit included in the medical light diffusion implant according to an embodiment of the present invention.

Referring to FIG. 6, the light source unit of the medical light diffusion implant may comprise a light source 601, a power supply unit 602, and a wire unit 603.

The light source 601 may emit the lights. The lights emitted by the light source 601 may include the monochromatic light. The lights emitted by the light source 601 may include the lasers. The lasers emitted by the light source 601 may include the light source having three properties of the lasers (i.e., monochromaticity, collimation, coherence). The light source 601 may emit the multi-wavelength light beam. The light source 601 may emit the lights without damages to the tissue. The light source 601 may emit the low power laser without the exothermic reaction. The light source 601 may include the light sources such as long pulse ruby lasers, helium neon lasers, argon lasers, and the like. The light source 601 may have effects for multiple tumor cells, hair growth, bore marrow hemoglobin synthesis, DNA/RNA synthesis of fibroblasts, wound healing and the like. The light source 601 may emit the low power laser. The light source 601 may maintain the tissue temperature at 43.5 degrees or less. The light source 601 may maintain the tissue temperature at 40 to 42 degrees. The light source 601 may maintain the tissue temperature at 39 degrees or less. The lights emitted by the light source 601 may include the cold laser which does not raise the temperature and the soft laser which does not cause damage to the tissue and may include the lights capable of photobiomodulation or photobiostimulation, and may include the light source which may cause the chemical change (photochemical effect) of the tissue by the lights regardless of the types of light sources such as lasers or LEDs.

The lights generated from the light source 601 may cause a sequential reaction followed as chromophore after absorbing photons of the lasers so as to generate a reaction in the tissue. Cytochrome C oxidase (COX) in mitochondria may cause the reaction by absorbing the laser photons. When COX absorbs the lasers, the electron transfer is activated in a respiratory circuit as a first response, followed by increasing nitric oxide (NO) production, which will adjust the reactive oxygen species (ROS) production and transmit weak heat to the surroundings. A second response may be followed by the first response, to increase DNA and RNA synthesis, to increase adenosine triphosphate (ATP) production. Thereby, various transcription factors are induced to affect cell proliferation and migration, resulting in regulating expressions of various materials such as cytokines, growth factors and inflammatory mediators, and increased oxygen saturation of the tissue. Additionally, nitric oxide produced by the low power laser may induce vasodilation, to allow delivering via NF-kB/AP-1 route with the reactive oxygen species to induce cell proliferation and promote the generation of various growth factors.

The light source 601 may emit the lights having the wavelength of 600 to 1200 nm in a red light region and a near infrared (NIR) region. The wavelengths below 600 nm are absorbed in hemoglobin and melanin to a large amount such that the energy is delivered to the portion other than a desired chromophore. The wavelengths of greater than 1200 nm have rapidly increased absorption as to water, which causes the problem in ensuring a sufficient depth required for the treatment. According to an embodiment, the light source 601 may emit the lights having the wavelength of 600 to 950 nm. According to an embodiment, the light source 601 may emit the lights having the wavelength of 600 to 700 nm for the tissue in a shallow depth, and the lights having the wavelength of 780 to 950 nm for the tissue in a deep region. According to an embodiment, the light source 601 may emit the lights having four peak regions (613.5-623.5 nm, 667.5-683.7 nm, 750.7-772.3 nm, 812.5-846.0 nm).

The light source 601 may comprise a single or plurality of LED elements. The light source 601 not limited to the LED, but may be formed of an element capable of emitting the lights.

The power supply unit 602 may generate energy required for the light source 601 to emit the lights. The energy may include electrical energy. The power supply unit 602 may include a piezoelectric element. The piezoelectric element may generate a current of 0.001 to 20 mA per masticatory motion. The piezoelectric element may generate a voltage of 3 to 10 V per the masticatory motion. The piezoelectric element may be located closely to the crown. The crown may transmit the pressure applied by the masticatory motion to the piezoelectric element. The piezoelectric element may be brought into close contact with the crown so as to convert the pressure due to the masticatory motion transferred from the crown into electric energy.

The power supply unit 602 may include a battery. The power supply unit 602 may store electrical energy and continuously supply the electrical energy to the light source 601. The power supply unit 602 may supply the electric energy to the light source 601 by receiving and charging the electric energy from an outside source. The power supply unit 602 may supply the electric energy to the light source 601 by receiving and charging electric energy through wireless charging.

The wire unit 603 may supply the energy of the power supply unit 602 to the light source 601. The wire unit 603 may connect the power supply unit 602 and the light source 601. A distance between the power supply unit 602 and the light source 601 may be set by the wire unit 603. The wire unit 603 may include electric wires and insulators surrounding and insulating the wires. The insulators may be made of a plastic material. The wire unit 603 may be made of a material having elasticity and flexibility. The wire unit 603 may be made of a material having a predetermined hardness.

Figure 7:
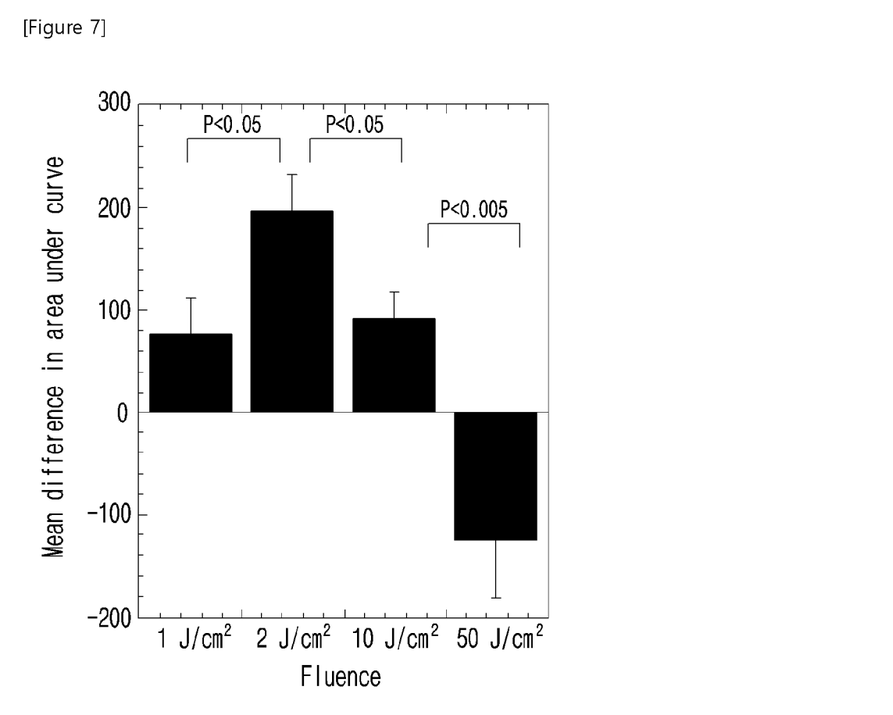
FIGS. 7 and 8 show a graph exhibiting the differences in cell recovery effects depending on the light dose.
Figure 8:
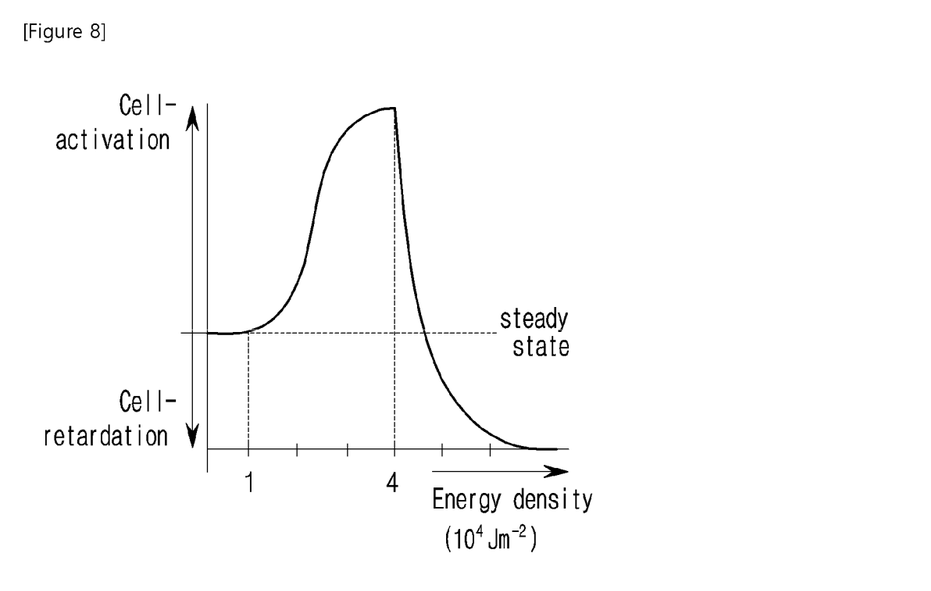

FIGS. 7 and 8 show a graph exhibiting the differences in cell recovery effects depending on the light dose.

Referring to FIGS. 7 and 8, when an output exceeds a certain level, the effect changes to a reversed result. Such graph shape is referred as a biphasic dose-response curve, i.e., "Arndt-Schulz" curve. In other words, it is known that the accurate adjustment of energy density and intensity is very important for ensuring the therapeutic effect because the therapeutic effect is reduced when exposing either lower or greater than the certain level of energy exhibiting the effects. Referring to the graph of FIG. 8, the light source of the present invention may generate the lights having an energy density of 2.5 to 4.5 ($10^4$ J/m$^2$).

Those skilled in the art will appreciate that the conceptions and specific embodiments disclosed is the foregoing description may be readily utilized as a basis for modifying or designing other embodiments for carrying out the same purposes of the present invention. Accordingly, the scope of the present invention should not be determined by the above-described embodiments, and should be determined by not only the appended claims but also their equivalents.

The invention claimed is:

1. A dental light diffusion implant, comprising:
   a socket including an inner space therein, capable of being fixed to a living body;
   a crown coupled with the socket to seal the socket; and
   an abutment including an inner space therein, configured to connect and fix the socket and the crown,
   wherein the socket is transmittable by lights, wherein a light source unit capable of emitting a light is provided within the inner space of the socket and within the inner space of the abutment,
   wherein the light source unit comprises a light source and a power supply unit to generate electrical energy, and
   wherein the power supply unit includes a piezoelectric element which contacts the crown to convert the pressure applied by masticatory motion into energy.

2. The dental light diffusion implant according to claim 1, wherein the socket comprises at least one through-hole to pass through inside and outside of the socket.

3. The dental light diffusion implant according to claim 2, wherein the through-holes are included as a plurality of holes.

4. The dental light diffusion implant according to claim 2, further comprising a shield film of a light-transmitting material to prevent foreign substances from entering into the socket.

5. The dental light diffusion implant according to claim 1, wherein the socket has at least a portion formed by a light-transmitting material.

6. The dental light diffusion implant according to claim 5, wherein the socket is entirely formed of the light-transmitting material.

7. The dental light diffusion implant according to claim 5, wherein the light-transmitting material comprises glass, ceramics or plastic.

8. The dental light diffusion implant according to claim 1, wherein the light source unit further comprises
   a wire unit to supply the electrical energy generated by the power supply unit to the light source.

9. The dental light diffusion implant according to claim 1, wherein the light source comprises an LED element.

10. The dental light diffusion implant according to claim 9, wherein the LED element has an output of 3000 mw or less.

11. The dental light diffusion implant according to claim 9, wherein the LED element emits lights having a wavelength of 600 to 700 nm.

12. The dental light diffusion implant according to claim 9, wherein the LED element emits lights having a wavelength of 780 to 950 nm.

13. The dental light diffusion implant according to claim 9, wherein the LED element generates the lights having an energy density of 2.5 to 4.5 ($10^4$ J/m$^2$).

* * * * *